US010166679B2

(12) United States Patent
Tanibayashi et al.

(10) Patent No.: US 10,166,679 B2
(45) Date of Patent: Jan. 1, 2019

(54) MOVEMENT ASSISTANCE DEVICE

(71) Applicant: Panasonic Corporation, Osaka (JP)

(72) Inventors: Hiroki Tanibayashi, Kyoto (JP);
Makoto Konishi, Osaka (JP);
Hiromichi Fujimoto, Nara (JP); Takuo
Wariishi, Osaka (JP)

(73) Assignee: Panasonic Corporation, Osaka (JP)

( * ) Notice: Subject to any disclaimer, the term of this
patent is extended or adjusted under 35
U.S.C. 154(b) by 0 days.

(21) Appl. No.: 15/501,973

(22) PCT Filed: Jun. 23, 2015

(86) PCT No.: PCT/JP2015/003138
§ 371 (c)(1),
(2) Date: Feb. 6, 2017

(87) PCT Pub. No.: WO2016/021103
PCT Pub. Date: Feb. 11, 2016

(65) Prior Publication Data
US 2017/0232617 A1 Aug. 17, 2017

(30) Foreign Application Priority Data

Aug. 8, 2014 (JP) ................. 2014-162479
Mar. 6, 2015 (JP) ................. 2015-045295

(51) Int. Cl.
A61H 3/00 (2006.01)
B25J 11/00 (2006.01)
(Continued)

(52) U.S. Cl.
CPC ............ B25J 11/00 (2013.01); A61F 5/0102
(2013.01); A61H 1/0244 (2013.01);
(Continued)

(58) Field of Classification Search
CPC ... A61F 5/028; A61F 5/026; A61H 2201/165;
A61H 3/00
(Continued)

(56) References Cited

U.S. PATENT DOCUMENTS 7,429,253 B2 * 9/2008 Shimada ............... A61F 5/0102
602/16
7,628,766 B1 * 12/2009 Kazerooni ............... A61F 5/00
601/35

(Continued)

FOREIGN PATENT DOCUMENTS

JP 2000-51289 2/2000
JP 2011-87926 5/2011
(Continued)

OTHER PUBLICATIONS

Extended European Search Report dated Jul. 14, 2017 in European Patent Application No. 15830732.2.
(Continued)

Primary Examiner — Steven M Marsh
(74) Attorney, Agent, or Firm — Wenderoth, Lind & Ponack, L.L.P.

(57) ABSTRACT

A movement assistance device includes: a back plate that is fitted onto the back of a wearer; a back frame that has an elongated shape and is supported by a rotating shaft fixed to the back plate so as to be rotatable in a plane parallel to the back plate; a side frame that is rotatably supported by a rotating shaft fixed to the back frame and parallel to the longitudinal direction of the back frame and extends from the back frame toward the vicinity of the side waist of the wearer; a thigh holding portion that is fitted onto the anterior thigh of the wearer; and a drive portion that is connected to each of the side frame and the thigh holding portion and generates force that increases the angle between the side frame and the thigh holding portion.

14 Claims, 16 Drawing Sheets

(51) Int. Cl.
 *A61H 1/02* (2006.01)
 *A61F 5/01* (2006.01)
 *B25J 19/00* (2006.01)
(52) U.S. Cl.
 CPC ............. *A61H 1/0292* (2013.01); *A61H 3/00* (2013.01); *A61H 3/008* (2013.01); *B25J 19/0091* (2013.01); *A61F 2005/0155* (2013.01); *A61H 2201/0192* (2013.01); *A61H 2201/1215* (2013.01); *A61H 2201/163* (2013.01); *A61H 2201/164* (2013.01); *A61H 2201/165* (2013.01); *A61H 2201/1619* (2013.01); *A61H 2201/1642* (2013.01); *A61H 2201/1645* (2013.01); *A61H 2201/1676* (2013.01); *A61H 2201/5069* (2013.01)
(58) Field of Classification Search
 USPC ...................................................... 602/16, 19
 See application file for complete search history.

(56) References Cited

U.S. PATENT DOCUMENTS

| | | | | |
|---|---|---|---|---|
| 8,568,344 | B2* | 10/2013 | Ferguson | A61H 3/00 602/16 |
| 8,968,222 | B2* | 3/2015 | Kazerooni | B25J 9/0006 224/265 |
| 9,707,146 | B2* | 7/2017 | Kwon | A61H 1/0262 |
| 2008/0161738 | A1 | 7/2008 | Giesen | |
| 2009/0137934 | A1* | 5/2009 | Seon | A61F 5/0123 602/19 |
| 2010/0036302 | A1* | 2/2010 | Shimada | A61F 5/0102 602/16 |
| 2010/0069806 | A1* | 3/2010 | Jinright | A61F 5/01 602/19 |
| 2012/0184881 | A1 | 7/2012 | Kobayashi et al. | |
| 2013/0331744 | A1 | 12/2013 | Kamon | |
| 2014/0051178 | A1 | 2/2014 | Niggel et al. | |

FOREIGN PATENT DOCUMENTS

| | | |
|---|---|---|
| JP | 2013-173190 | 9/2013 |
| JP | 2014-61113 | 4/2014 |
| JP | 5526444 | 4/2014 |
| WO | 2011/036906 | 3/2011 |
| WO | 2012/070244 | 5/2012 |
| WO | 2012/171000 | 12/2012 |

OTHER PUBLICATIONS

International Search Report dated Jul. 28, 2015 in International (PCT) Application No. PCT/JP2015/003138.

* cited by examiner

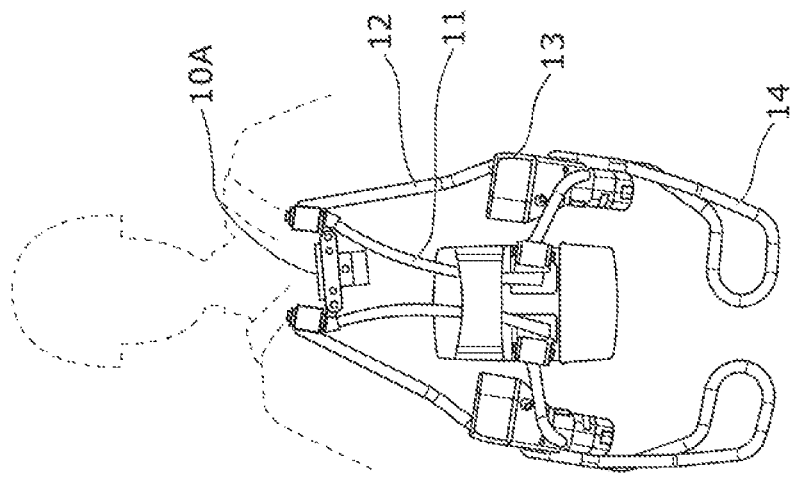
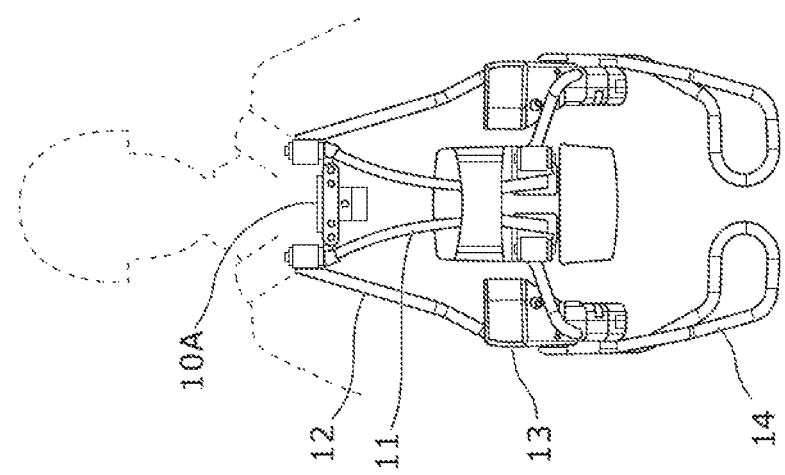

ical Field

The present invention relates to movement assistance devices.

BACKGROUND ART

There are movement assistance devices that are fitted onto persons and assist movements of the persons fitted with the movement assistance devices (hereinafter, referred to as wearers). Specifically, for example, when the wearers move to lift a heavy object, the movement assistance device generates part of the force required for the movement to reduce the force to be generated by the wearers. In this way, the movement assistance devices assist a movement of the wearers by covering part of the force to be generated by the wearers.

The movement assistance devices are roughly divided into two types: one is a grounded type, and the other is a non-grounded type. The grounded-type movement assistance device is provided in contact with the ground. The wearer who rides on the movement assistance device is assisted by the movement assistance device. Since the wearer rides on the movement assistance device placed on the ground, the wearer does not need to support the weight of the movement assistance device. The grounded-type movement assistance device is used in an application for assisting a movement with relatively large or complicated force.

In contrast, the non-grounded-type movement assistance device is not in contact with the ground and is fitted onto part of the body of the wearer. The wearer who is fitted with the movement assistance device is assisted by the movement assistance device. Since the movement assistance device is fitted onto the body of the wearer, the wearer needs to support the weight of the movement assistance device. Furthermore, the non-grounded-type movement assistance device is fitted by, for example, being slung over the shoulders of the wearer or being wound around the waist of the wearer, and therefore is likely to limit a free movement of the wearer compared with the case of the grounded-type movement assistance device. The non-grounded-type movement assistance device is used in an application for simpler and easier assistance on the movement with relatively small force.

Japanese Patent No. 5526444 discloses a non-grounded-type movement assistance device. This movement assistance device assists forward bending action of the wearer.

The movement assistance device disclosed in Japanese Patent No. 5526444 includes a back frame and the like formed from a rigid member in order to maintain the structure of the movement assistance device. The rigid member maintains the form, thereby limiting a free movement of the wearer.

The present invention is conceived in order to solve the aforementioned existing problem and has an object to provide a movement assistance device that assists a movement of a wearer while maintaining the degree of freedom of the movement.

SUMMARY OF THE INVENTION

In order to solve the aforementioned problem, a movement assistance device according to an aspect of the present invention includes: a back plate that is fitted onto a back of a wearer; a back frame that has an elongated shape and is supported by a rotating shaft so as to be rotatable in a plane parallel to the back plate, the rotating shaft being fixed to the back plate; a side frame that is rotatably supported by a rotating shaft and extends from the back frame toward a vicinity of a side waist of the wearer, the rotating shaft being fixed to the back frame and parallel to a longitudinal direction of the back frame; a thigh holding portion that is fitted onto an anterior thigh of the wearer; and a drive portion that is connected to each of the side frame and the thigh holding portion and generates force that increases an angle between the side frame and the thigh holding portion.

With this, the movement assistance device can independently rotate the back frame with respect to the back plate and rotate the side frame with respect to the back frame according to the movement of the wearer. Thus, even when the wearer moves to twist his or her upper body or moves to swing his or her body so as to change the height of his or her left and right shoulders, the movement assistance device can follow the movement of the wearer without restricting the movement and, as necessary, assist the movement. Thus, the movement assistance device is capable of assisting the movement of the wearer while maintaining the degree of freedom of the movement.

For example, the side frame is rotatably supported by the back frame at both ends of the back frame and rotates around an axis connecting the both ends of the back frame as the rotating shaft.

With this, the side frame is more stably supported with respect to the back frame and can follow the movement of the wearer. Thus, the movement assistance device is capable of assisting the movement of the wearer while maintaining the degree of freedom of the movement.

For example, the movement assistance device further includes a waist plate that is connected to the back plate via a flexible member and fitted onto a posterior waist of the wearer, and a lower end of the back frame abuts the waist plate.

With this, since the lower end of the back frame abuts the waist plate, it is possible to prevent the lower end of the back frame from directly contacting the waist of the wearer. Thus, the back frame can rotate more smoothly, and the discomfort for the wearer, such as pressure and pain, upon fitting can be reduced.

For example, the waist plate includes a restricting portion that restricts an angle of rotation of the back frame with respect to the back plate to an angle within a predetermined range.

Thus, with the angle of rotation of the back frame set within a predetermined range, the drive portion and the thigh holding portion connected to the back frame via the side frame can be maintained in positions that are not away from the body of the wearer. Thus, the movement assistance device is capable of assisting the movement of the wearer while maintaining the degree of freedom of the movement.

For example, the back frame includes a restoring mechanism that, when an angle of rotation between the back frame and the side frame deviates from a predetermined range, changes the angle of rotation so that the angle of rotation falls within the predetermined range.

With this, in the case where the posture of the wearer changes from a predetermined posture (for example, the standing posture) and then returns to the predetermined posture, the movement assistance device can return the angle of rotation of each of the back frame and the side frame to that for the original, predetermined posture. In the case where the wearer changes his or her posture and then returns to the original posture, the angle of rotation of the movement assistance device returns to the original angle as well, and thus the wearer does not need to perform other special movements or operations. Thus, the movement assistance device is capable of assisting the movement of the wearer while maintaining the degree of freedom of the movement.

For example, the movement assistance device further includes a belt that extends from the back plate over an anterior surface of a body of the wearer to the waist plate and is connected to the waist plate, and the drive portion generates the force that increases the angle between the side frame and the thigh holding portion to provide standing force to the wearer via the back frame, the back plate, and the shoulder belt, the standing force being force for raising an upper body of the wearer to an upright position.

With this, the movement assistance device transmits, to the belt and so on, force generated by the drive portion, to raise the upper body of the wearer to an upright position, and thus assists the movement of the wearer.

For example, the drive portion provides the standing force to the wearer in a state where the movement assistance device is fitted onto the wearer without contacting a ground.

With this, the wearer is fitted with the movement assistance device in such a manner as to support the weight of the movement assistance device, and the movement of the wearer is assisted by the movement assistance device. Thus, the movement assistance device is capable of simpler and easier assistance on the movement of the wearer while maintaining the degree of freedom of the movement.

For example, the shoulder belt includes: a left shoulder belt that extends from the back plate over a left shoulder and the anterior surface of the body of the wearer to the waist plate and is connected to the waist plate; a right shoulder belt that extends from the back plate over a right shoulder and the anterior surface of the body of the wearer to the waist plate and is connected to the waist plate; and an attaching portion that detachably joins the left shoulder belt and the right shoulder belt together at the anterior surface of the body of the wearer.

With this, in the movement assistance device, the force for movement assistance is more efficiently transmitted to the body of the wearer, and thus the movement assistance performance improves, and it is possible to reduce wasteful force generation to reduce power consumption. Furthermore, the left shoulder belt and the right shoulder belt can be attached and detached by the attaching portion, allowing the wearer to easily wear and remove the movement assistance device.

For example, the shoulder belt includes: a shoulder belt main portion; and a first adjustment portion that is detachably attached to a surface of the shoulder belt main portion, the surface facing the wearer in a state where the movement assistance device is fitted onto the wearer.

With this, the degree of fitting tightness between the shoulder belt of the movement assistance device and the body of the wearer is further increased. This further improves the movement assistance performance of the movement assistance device and further improves the advantageous effect of reducing power consumption.

For example, the first adjustment portion is a cushioning member.

With this, it is possible to further improve the advantageous effect such as an improvement in the movement assistance performance of the movement assistance device, a reduction in the power consumption, or impact mitigation.

Furthermore, the advantageous effect of improving the comfort for the wearer who is fitted with the movement assistance device is produced.

For example, the movement assistance device further includes a waist belt that has a band shape and is connected to the waist plate and fitted around a waist of the wearer, and the waist belt includes: a waist belt main portion; and a second adjustment portion that is detachably attached to a surface of the waist belt main portion, the surface facing the wearer in a state where the movement assistance device is fitted onto the wearer.

With this, the degree of fitting tightness between the waist belt of the movement assistance device and the body of the wearer is further increased. This further improves the movement assistance performance of the movement assistance device and further improves the advantageous effect of reducing power consumption.

For example, the second adjustment portion is a cushioning member.

With this, it is possible to improve the advantageous effect such as an improvement in the movement assistance performance of the movement assistance device, a reduction in the power consumption, or impact mitigation. Furthermore, the advantageous effect of improving the comfort for the wearer who is fitted with the movement assistance device is produced.

For example, the thigh holding portion includes: a thigh fitting portion that is fitted onto a thigh of the wearer; and a third adjustment portion that is detachably attached to a surface of the thigh fitting portion, the surface facing the wearer in a state where the movement assistance device is fitted onto the wearer.

With this, the degree of fitting tightness between the thigh holding portion of the movement assistance device and the body of the wearer is further increased. This further improves the movement assistance performance of the movement assistance device and further improves the advantageous effect of reducing power consumption.

For example, the third adjustment portion is a cushioning member.

With this, it is possible to improve the advantageous effect such as an improvement in the movement assistance performance of the movement assistance device, a reduction in the power consumption, or impact mitigation. Furthermore, the advantageous effect of improving the comfort for the wearer who is fitted with the movement assistance device is produced.

Advantageous Effects of Invention

The movement assistance device according to an aspect of the present invention is capable of assisting a movement of a wearer while maintaining the degree of freedom of the movement.

BRIEF DESCRIPTION OF DRAWINGS

FIGS. 8(a) and 8(b) illustrate the second exemplary attitude of a movement assistance device according to Embodiment 1.

DESCRIPTION OF EMBODIMENTS

Note that each of the following embodiments describes a specific preferred example of the present invention. The numerical values, shapes, materials, structural elements, the arrangement and connection of the structural elements, steps, the processing order of the steps etc. shown in the following embodiments are mere examples, and are not intended to limit the scope of the present invention. Furthermore, among the structural elements in the following embodiments, structural elements not recited in the independent claim indicating the broadest concept of the present invention are described as arbitrary structural elements of a more preferable embodiment.

Note that the same structural elements are assigned the same reference signs, and overlapping description may be omitted.

Embodiment 1

In the present embodiment, a movement assistance device that improves the degree of freedom of a movement of a wearer will be described.

Figure 1:
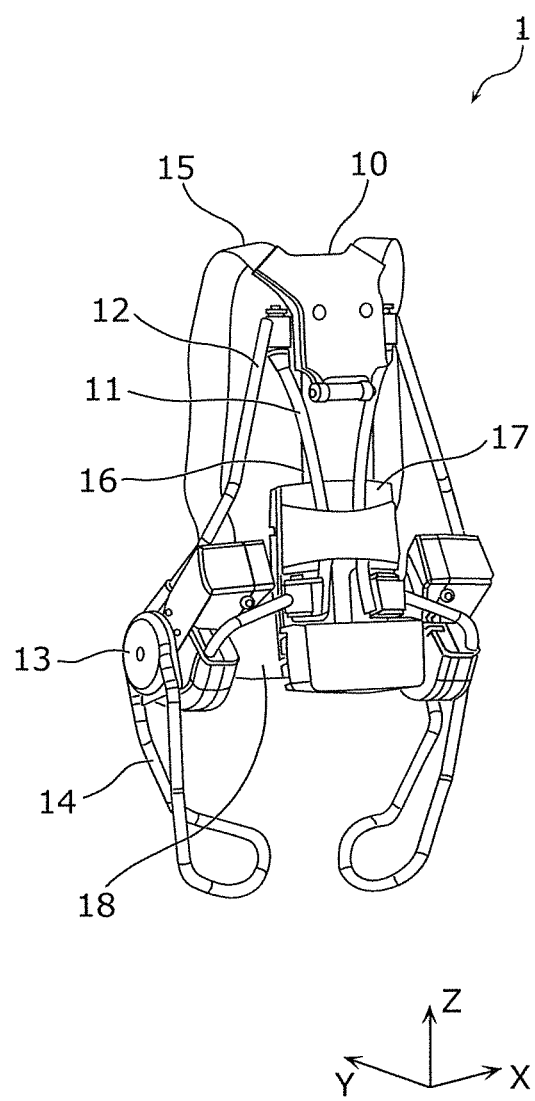
FIG. 1 is an external perspective view of a movement assistance device according to Embodiment 1.
Figure 2:
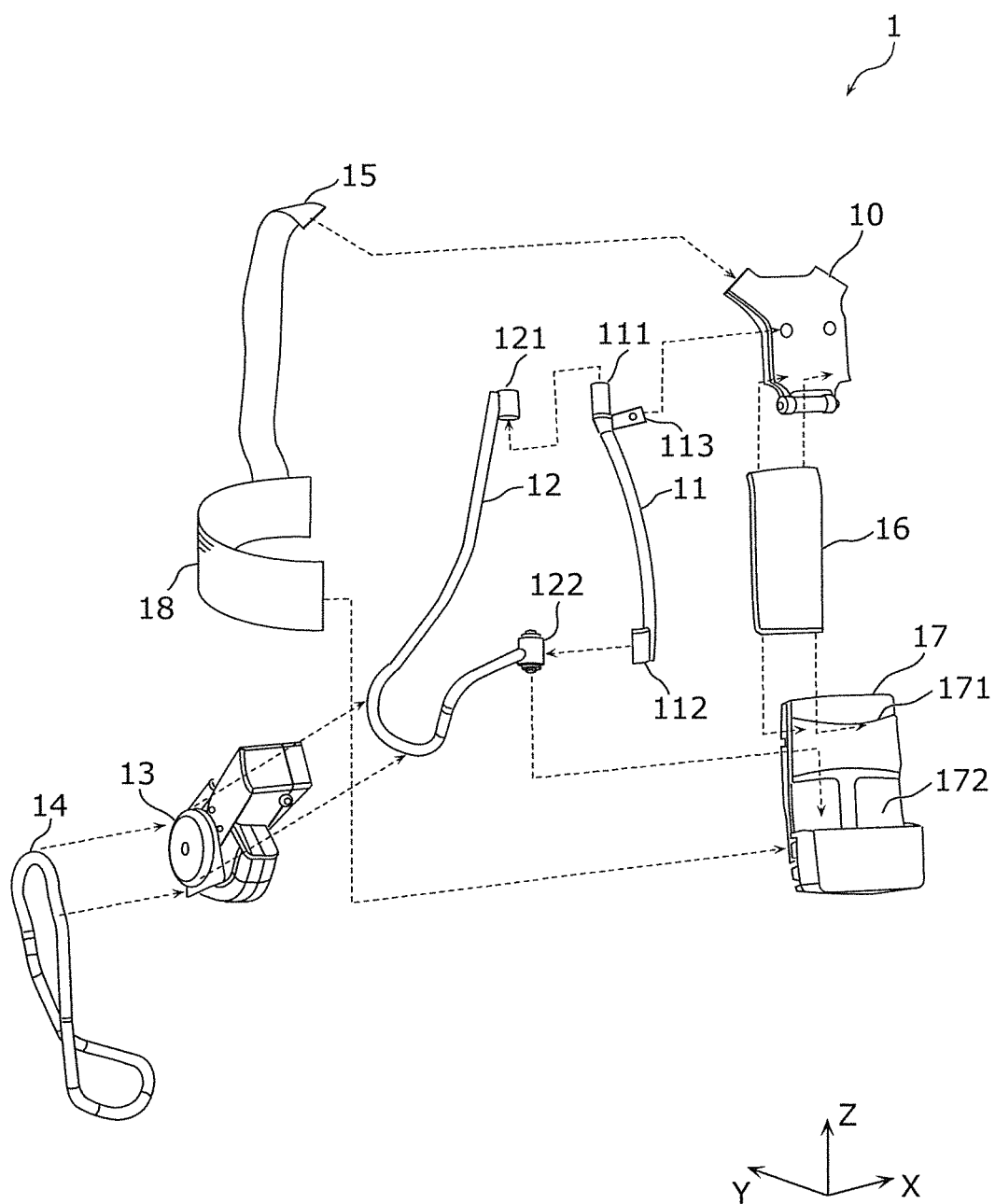
FIG. 2 is an exploded perspective view of a movement assistance device according to Embodiment 1.

FIG. 1 is an external perspective view of a movement assistance device 1 according to the present embodiment. FIG. 2 is an exploded perspective view of the movement assistance device 1 according to Embodiment 1. Note that the following description includes description using the coordinate axes indicated in the drawings. In such description, there are cases where the positive direction of the Z axis is referred to as upward, and the negative direction of the Z axis is referred to as downward.

As illustrated in FIG. 1 and FIG. 2, the movement assistance device 1 includes a back plate 10, a back frame 11, a side frame 12, a drive portion 13, a thigh holding portion 14, a shoulder belt 15, a connecting belt 16, a waist plate 17, and a waist belt 18.

The back plate 10 is a board-shaped rigid member that is fitted onto the back of the wearer. The back plate 10 is positioned on the back of the wearer (specifically, in substantially the middle of the back) when the movement assistance device 1 is fitted onto the wearer. The back plate 10 is substantially fixed at a position on the back of the wearer by the shoulder belt 15, and the position and the angle of the back plate 10 vary according to the movement of the back of the wearer.

The back plate 10 has a rotating shaft fixed to the back plate 10 and supports the back frame 11 via the rotating shaft. The rotating shaft is, for example, a hole 102 formed in part of the back plate 10. Note that the rotating shaft may be any element as long as it rotatably supports the back frame 11 and may be, for example, a recess or projection formed in or on part of the back plate 10.

The back frame 11 is a rod-shaped rigid member that is fitted onto the back of the wearer, and is specifically a rigid member that is in the shape of a straight line or in the shape of a curved line. The back frame 11 is rotatably supported by the rotating shaft fixed to the back plate 10. The back frame 11 is supported only by the above-described rotating shaft, and is therefore suspended in the direction of gravity acting on the back frame 11 and the like. Furthermore, the back frame 11 passes through a hollow part of the tubular structure of a restricting portion 171 and abuts the waist plate 17 at the lower end.

The back frame 11 includes two first frame portions (one on each side), each having rotation supporting portions 111 and 112 and a bearing portion 113 (see, e.g., FIGS. 1, 2, 4, and 5).

The rotation supporting portions 111 and 112 of each of the two first frame portions are support members that rotatably support a respective (different) one of two second frame portions of the side frame 12. The rotation supporting portions 111 and 112 have a rotating shaft. For example, the rotation supporting portions 111 and 112 are provided at the both ends of the back frame 11. Specifically, the rotation supporting portion 111 is provided at the upper end of the back frame 11, and the rotation supporting portion 112 is provided at the lower end of the back frame 11. Note that although the configuration illustrated in FIG. 1 and FIG. 2 includes two rotation supporting portions 112, the number of rotation supporting portions 112 may be one or may be three or more. In addition, the rotating shaft may be a single rotating shaft or may be two or more rotating shafts. Providing two or more rotating shafts is advantageous in increasing the design flexibility of the device structure of the movement assistance device 1.

The bearing portion 113 is supported by the back plate 10 via the rotating shaft. The bearing portion 113 has a hole 114 and is supported by the back plate 10 using the hole 114 as a rotating shaft. Note that the hole 114 may be any element as long as it functions as a rotating shaft and may be, for example, a recess or projection in or on part of the back frame 11.

The side frame 12 is a rigid member extending from the back frame 11 to the vicinity of the side waist of the wearer. The side frame 12 is rotatably supported by the rotating shaft fixed to the back frame 11. The side frame 12 may include a rod-shaped member curved as illustrated in FIG. 1 and FIG. 2 or may include a board-shaped member.

Each of the two second frame portions of the side frame 12 includes bearing portions 121 and 122. The bearing portions 121 and 122 are respectively attached to the rotation supporting portions 111 and 112 of a respective (different) one of the two first frame portions of the back frame 11 so as to rotate using the rotation supporting portions 111 and 112 as the rotating shaft.

The drive portion 13 is attached to part of the side frame 12 that is positioned in the vicinity of the side waist of the wearer.

The drive portion 13 is a driving device that is fitted onto the side waist of the wearer. Specifically, the drive portion 13 includes a motor, a power supply for driving the motor, and a sensor. The drive portion 13 is connected to each of the side frame 12 and the thigh holding portion 14 and generates force that increases the angle between the side frame 12 and the thigh holding portion 14. In other words, the drive portion 13 generates rotational force in the direction of increasing the angle between the side frame 12 and the thigh holding portion 14. The sensor of the drive portion 13 is an angle sensor that detects an angle between the side frame 12 and the thigh holding portion 14 and is, for example, implemented as an encoder.

The thigh holding portion 14 is a rigid member that is fitted onto the thigh of the wearer. The thigh holding portion 14 may include a rod-shaped member curved as illustrated in FIG. 1 and FIG. 2 or may include a board-shaped member. The thigh holding portion 14 is connected to the drive portion 13. In other words, the thigh holding portion 14 and the side frame 12 join together via the drive portion 13.

The thigh holding portion 14 is fitted onto the thigh of the wearer and thus substantially fixed to the thigh. When the drive portion 13 is driven in the state where the thigh holding portion 14 is substantially fixed to the thigh of the wearer, rotational force is generated to cause the side frame 12 to rise with the thigh holding portion 14 fixed in position, assisting the wearer in moving to stretch his or her hip.

The shoulder belt 15 is a band-shaped flexible member. The shoulder belt 15 is connected to the back plate 10 and extends from the back plate 10 over the shoulder and the anterior surface of the body of the wearer to the waist belt 18 to which the shoulder belt 15 is connected. The wearer is fitted with the movement assistance device 1 by draping the shoulder belt 15 over his or her shoulder so as to carry the movement assistance device 1 on his or her back.

The connecting belt 16 is a band-shaped flexible member and connects the back plate 10 and the waist plate 17 with each other. In the connecting belt 16, a direction connecting the back plate 10 and the waist plate 17 is referred to as a longitudinal direction. The connecting belt 16 maintains the distance in the longitudinal direction between the back plate 10 and the waist plate 17 within the length of the connecting belt 16, and allows the distance in the longitudinal direction to be reduced. Furthermore, the connecting belt 16 allows the relative position and angle between the back plate 10 and the waist plate 17 to change according to the posture of the wearer.

The waist plate 17 is a rigid member that is fitted onto the posterior waist of the wearer. The waist plate 17 is connected to the connecting belt 16 which joins the waist plate 17 and the back plate 10 together. Furthermore, the connecting belt 16 maintains the distance between the waist plate 17 and the back plate 10. The lower end of the back frame 11 abuts the waist plate 17.

The waist plate 17 includes the restricting portion 171 and an abutting portion 172.

The restricting portion 171 restricts the angle of rotation of the back frame 11 with respect to the back plate 10 to an angle within a predetermined range. The restricting portion 171 is a tubular rigid member, and the back frame 11 passes through the hollow part of the tube. With this, the angle of rotation of the back frame 11 is restricted.

The abutting portion 172 is where the lower end of the back frame 11 abuts the waist plate 17. The abutting portion 172 may be a member substantially the same as the waist plate 17 or may be one formed by applying a cushion material to the surface of the member. The cushion material can mitigate the impact that the back frame 11 has upon abutting the abutting portion 172.

The waist belt 18 is a band-shaped flexible member fitted around the waist of the wearer. The waist belt 18 is connected to part of the waist plate 17 and wound one time around the waist of the wearer until it is connected to another part of the waist plate 17. Note that an attaching and detaching mechanism may be provided on part of the waist belt 18 so that the wearer can easily put on and take off the movement assistance device 1.

In addition, the shoulder belt 15, the connecting belt 16, and the waist belt 18 may each include a mechanism for length adjustment. Note that the shoulder belt 15 and the waist belt 18 may be collectively referred to as a belt.

Note that each of the back frame 11 and the side frame 12 may be a solid rod or may be a hollow pipe. Furthermore, the cross-sectional shape of the back frame 11 and the side frame 12 can be any shape such as a circle, rectangle, or triangle. Use of hollow pipes as the back frame 11 and the side frame 12 is advantageous in terms of weight reduction compared with the use of solid rods. When these frames have circular cross-sections, the wearer does not come into contact with corners, and thus it is possible to reduce the discomfort for the wearer, such as pressure and pain, upon fitting.

Figure 4A:
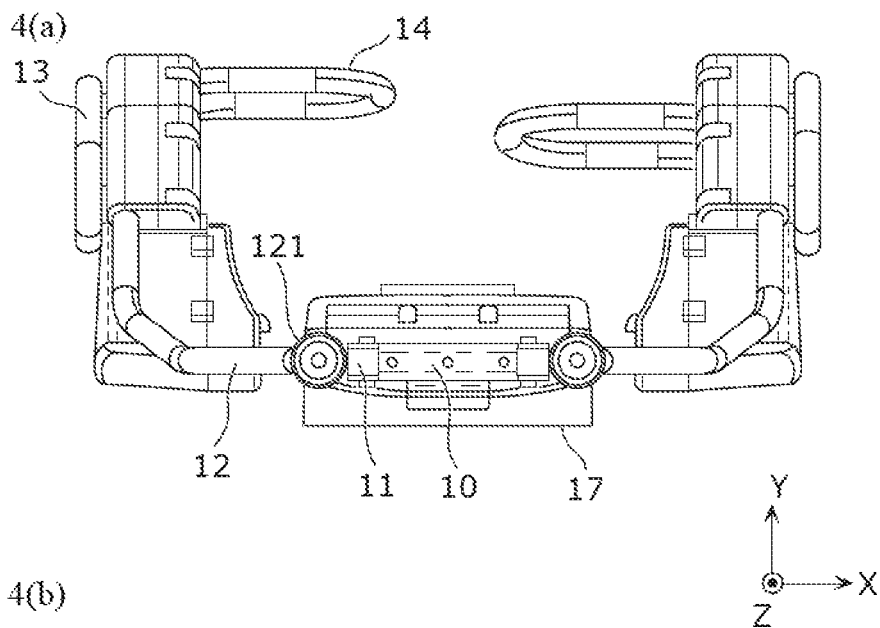
FIGS. 4(a) and 4(b) illustrate rotation of a side frame with respect to a back frame according to Embodiment 1.
Figure 4B:
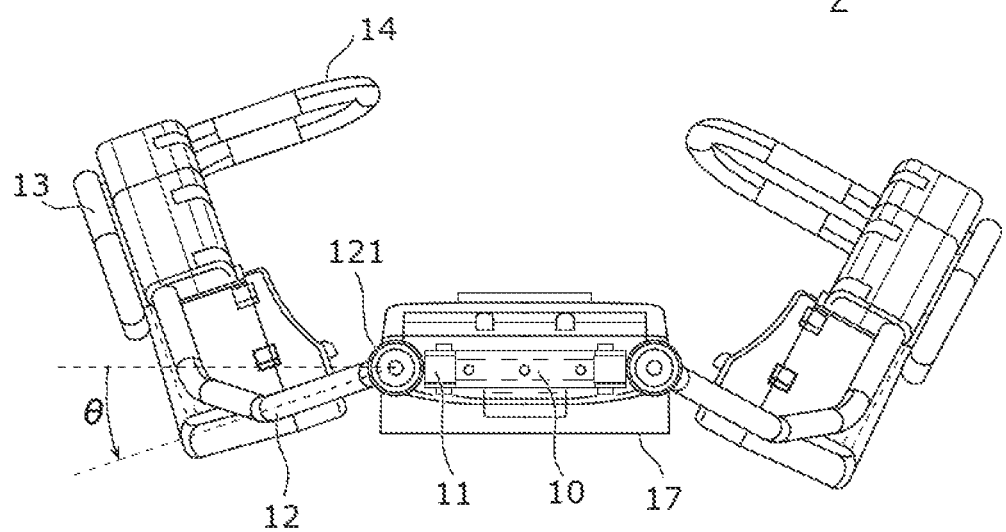

Note that the rotation of the back frame 11 with respect to the back plate 10 and the rotation of the side frame 12 with respect to the back frame 11 can be independent of each other. In other words, as illustrated in FIGS. 4(a) and 4(b), the two first frame portions of the back frame 11 rotate independently from each other, and the two second frame portions of the side frame 12 rotate independently from each other. Thus, it is possible to improve the degree of freedom of the movement of the wearer.

In the movement assistance device 1, the drive portion 13 generates force that increases the angle between the side frame 12 and the thigh holding portion 14, and thus standing force for raising the upper body of the wearer to an upright position is provided to the wearer via the back frame 11, the back plate 10, and the shoulder belt 15.

Note that the movement assistance device 1 is a non-grounded type movement assistance device that provides the above-described standing force to the wearer in the state where the movement assistance device is fitted onto the wearer without contacting the ground.

Figure 3:
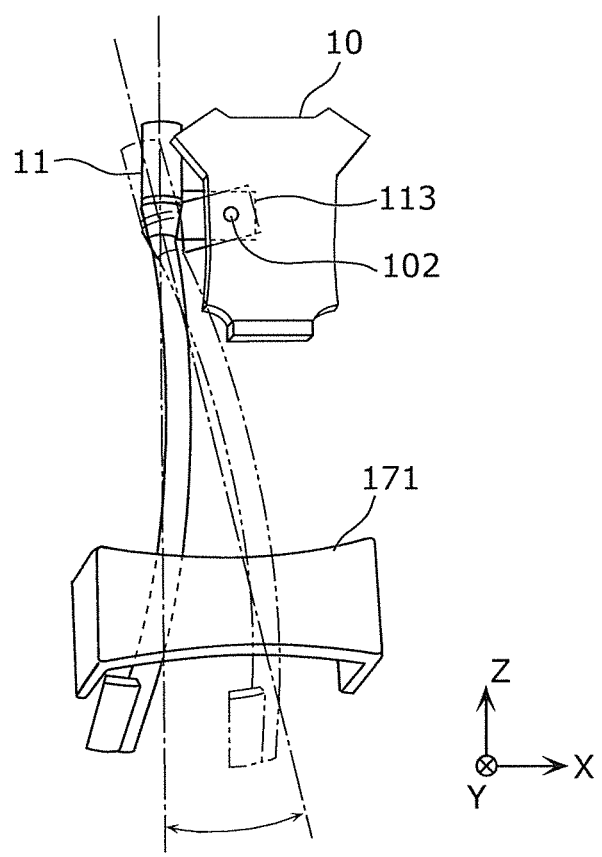
FIG. 3 illustrates rotation of a back frame with respect to a back plate according to Embodiment 1.

FIG. 3 illustrates rotation of the back frame 11 with respect to the back plate 10 according to the present embodiment. Note that in FIG. 3, illustration of structural elements other than the back plate 10, the back frame 11, and the restricting portion 171 is omitted.

As illustrated in FIG. 3, the back frame 11 can rotate around the rotating shaft 102 fixed to the back plate 10. Since the back frame 11 is supported only by the rotating shaft 102, external force exerted on the back frame 11 rotates the back frame 11. For example, when the wearer twists his or her body, external force in the X direction is applied to the back frame 11. As a result, the back frame 11 rotates until no external force acts on the back frame 11. When the back plate 10 is tilted compared with the attitude illustrated in FIG. 3 due to a change in the posture of the wearer, the back frame 11 rotates until the back frame 11 reaches a position at which the back frame 11 is supported by the rotating shaft 102 and parallel to the direction of gravity due to the gravity.

In this case, the range of rotation of the back frame 11 is restricted by the restricting portion 171. Since the back frame 11 passes through the hollow part of the tubular restricting portion 171, the range of rotation of the back frame 11 is restricted to prevent the back frame 11 from rotating to the position at which the back frame 11 is detached from the restricting portion 171. Thus, it is possible to prevent the back frame 11 from rotating to an unintended position.

FIGS. 4(a) and 4(b) illustrate rotation of the side frame 12 with respect to the back frame 11 according to the present embodiment. FIGS. 4(a) and 4(b) are top views of the movement assistance device 1 as viewed from the top surface (from the positive side of the Z direction).

FIG. 4(a) illustrates a reference position of the side frame 12 with respect to the back frame 11. FIG. 4(a), the back frame 11 and part of the side frame 12 that connects to the back frame 11 are included in the plane including the back plate 10. At this time, the angle of rotation of the side frame 12 with respect to the back frame 11 is referred to as zero.

FIG. 4(b) illustrates a state resulting from the side frame 12 rotating through an angle θ with respect to the back frame 11. When the side frame 12 rotates with respect to the back frame 11, the drive portion 13 and the thigh holding portion 14, etc., connected to the side frame 12 also rotate together with the side frame 12.

In this way, the side frame 12 rotates with respect to the back frame 11, and thus the degree of freedom of the movement of the wearer is improved. For example, when the wearer is about to assume a posture including twisting his or her upper body leftward and stretching his or her left arm backward, the side frame 12 rotates in the direction in which the above θ increases. With this, the wearer can make his or her intended movement without being hindered by the movement assistance device 1.

Note that a rotating mechanism including the bearing portions 121 and 122 of the side frame 12 and the rotation supporting portions 111 and 112 of the back frame 11 may include a restoring mechanism that generates a restoring force for allowing the angle of rotation θ to approach a predetermined range or a predetermined value when the angle of rotation θ deviates from the predetermined range or the predetermined value. With this, when the angle θ is changed by force applied by the wearer, the rotation occurs according to the force, and when the wearer stops applying the force, the restoring force allows the angle θ to approach the predetermined range or the predetermined value. Note that the predetermined range may be set to the range of from plus 10 degrees to minus 10 degrees, for example. The predetermined value may be set to zero, for example. The restoring mechanism may be implemented as a rubber bush, for example.

Figure 5:
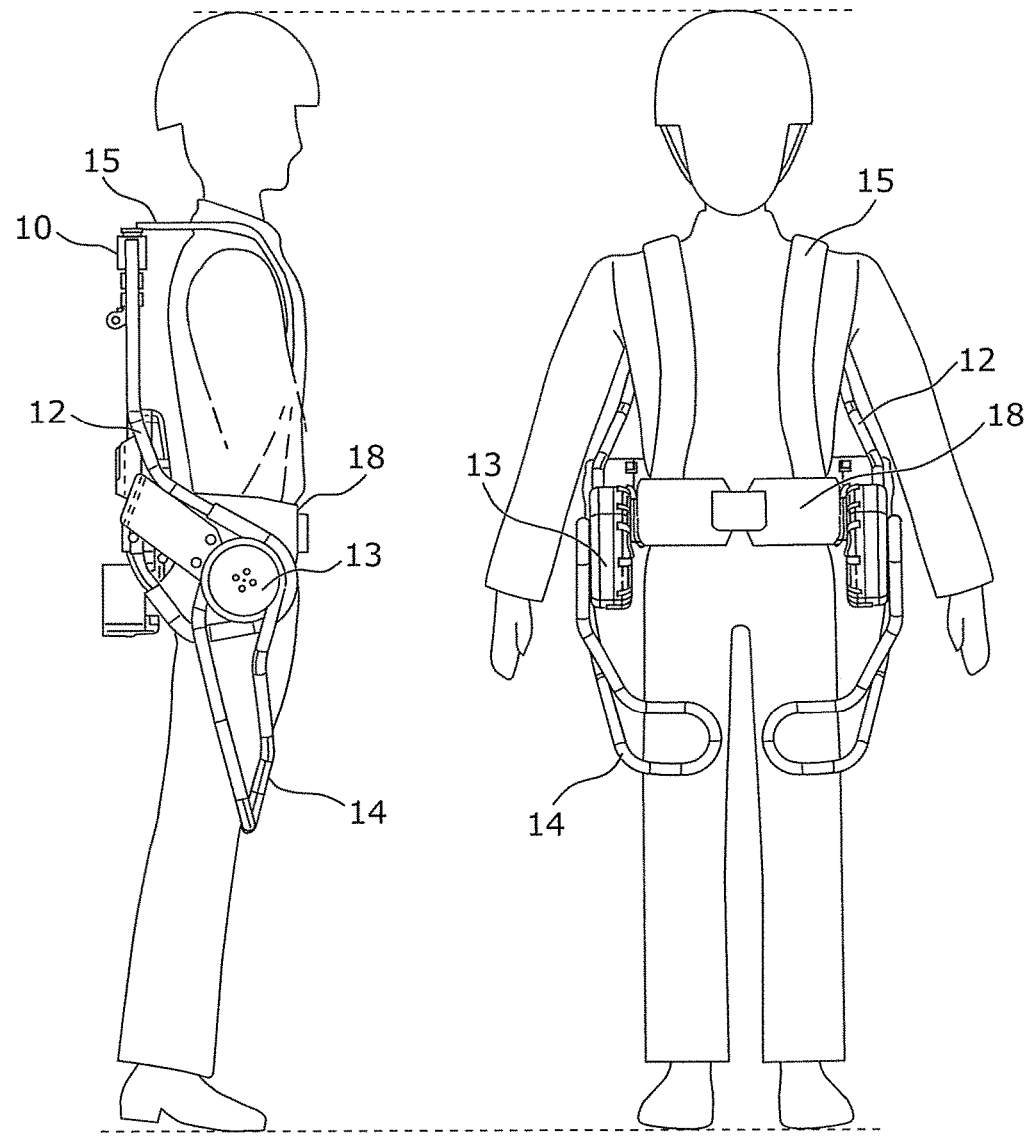
FIG. 5 is side and front views of a movement assistance device according to Embodiment 1.

FIG. 5 is side and front views of the movement assistance device 1 according to the present embodiment. FIG. 5 illustrates the wearer fitted with the movement assistance device 1 and assuming a standing posture.

As illustrated in FIG. 5, the wearer is fitted with the movement assistance device 1 by carrying the movement assistance device 1 on his or her back using the shoulder belt 15. The back plate 10 is positioned in the vicinity of the back of the wearer, and the waist plate 17 is positioned in the vicinity of the posterior waist of the wearer. The drive portion 13 is positioned at the side waist of the wearer, and the thigh holding portion 14 is positioned in contact with the thigh of the wearer.

Figure 6:
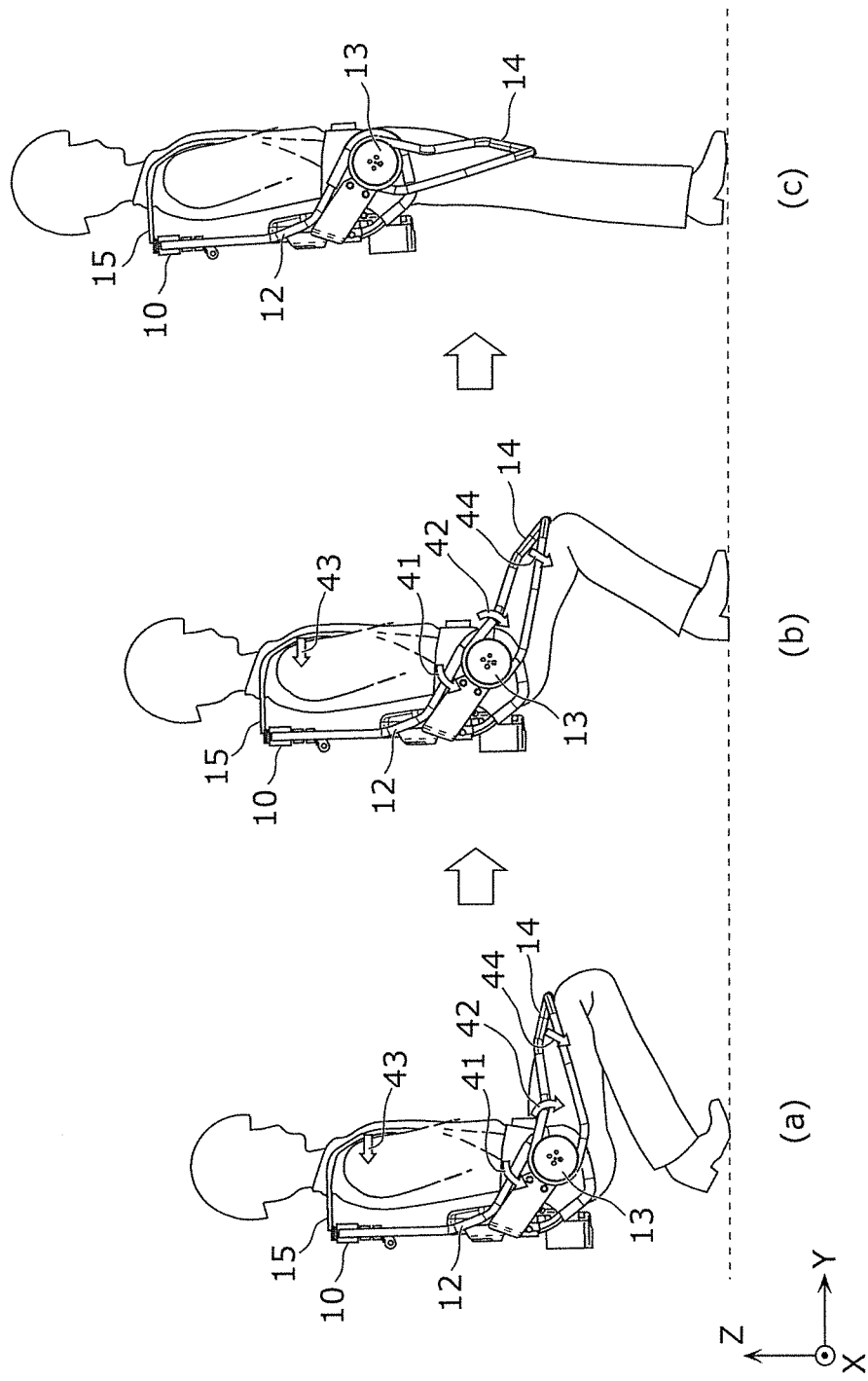
FIG. 6 illustrates movement assistance provided by a movement assistance device according to Embodiment 1.

FIG. 6 illustrates movement assistance provided by the movement assistance device 1 according to the present embodiment.

With reference to FIG. 6, description is given on the movement assistance provided by the movement assistance device 1 from when the wearer assumes a squatting posture until when the wearer assumes a standing posture.

In FIG. 6, (a) illustrates the state where the wearer assumes a squatting posture. In the state (a) in FIG. 6, the wearer starts a movement to assume a standing posture with his or her own strength. Specifically, the wearer moves to stretch his or her bent knees and hip a little.

At this time, the sensor of the drive portion 13 detects rotation that increases the angle between the side frame 12 and the thigh holding portion 14. When such rotation is detected, the motor of the drive portion 13 generates rotational force 41 and rotational force 42 in the direction of increasing the angle between the side frame 12 and the thigh holding portion 14.

When the drive portion 13 generates the rotational force 41, the side frame 12 attempts to move in the direction of pulling the upper body of the wearer backward. This force is transmitted to the shoulder belt 15 via the back frame 11 and the back plate 10 and acts on the wearer as force 43 that pushes the shoulder or the chest of the wearer backward from the front side.

When the rotational force 42 is generated, the rotational force 42 acts on the wearer as force 44 of the thigh holding portion 14 pushing the thigh of the wearer downward.

As described above, the movement assistance device 1 applies the force 43 and the force 44 to the wearer, and thus the wearer only needs to generate force less than in the case where the movement assistance device 1 is not used, to change from the squatting posture to a half-sitting posture.

In FIG. 6, (b) illustrates the state where the wearer assumes the half-sitting posture. Also in the state (b) in FIG. 6, the drive portion 13 generates the rotational force 41 and the rotational force 42, as in the state (a) in FIG. 6.

The rotational force 41 generated by the drive portion 13 acts on the wearer as the force 43 that pushes the shoulder or the chest of the wearer backward from the front side, as in the state (a) in FIG. 6.

In the meantime, the rotational force 42 acts on the wearer as force that pushes the surface of the thigh of the wearer vertically downward, that is, the force 44 that pushes the thigh of the wearer downward but slightly backward.

As described above, the movement assistance device 1 applies the force 43 and the force 44 to the wearer, and thus the wearer only needs to generate force less than in the case where the movement assistance device 1 is not used, to change from the half-sitting posture to the standing posture.

In FIG. 6, (b) illustrates the state where the wearer assumes the standing posture. In the state (c) in FIG. 6, when the angle between the side frame 12 and the thigh holding portion 14 detected by the sensor of the drive portion 13 is equal to the angle defined as the angle of the wearer assuming the standing posture, the motor of the drive portion 13 stops generating the rotational force 41 and the rotational force 42. Note that thereafter, the motor of the drive portion 13 may subsequently generate force suited to maintain the angle between the side frame 12 and the thigh holding portion 14 or may stop force generation.

In the manner described above, the movement assistance device 1 applies the force 43 and the force 44 to the wearer, so that the wearer changes from the squatting posture to the standing posture via the half-sitting posture with assistance of the movement assistance device 1 without using his or her own strength much.

Figure 7:
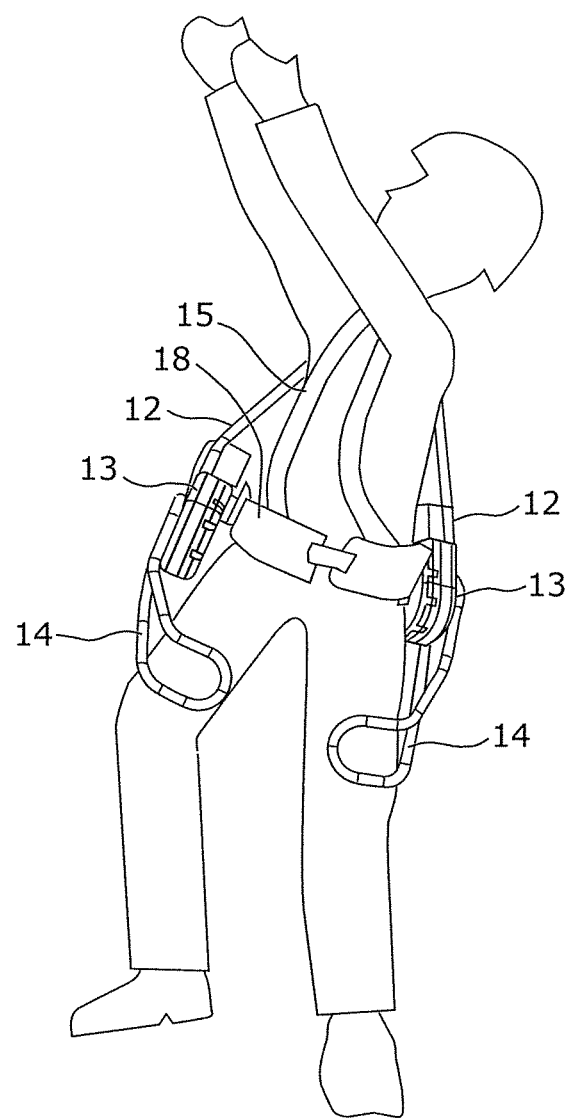
FIG. 7 illustrates the first exemplary attitude of a movement assistance device according to Embodiment 1.

FIG. 7 illustrates the first exemplary attitude of the movement assistance device 1 according to the present embodiment. The wearer illustrated in FIG. 7 is fitted with the movement assistance device 1 and assumes a posture including twisting his or her upper body while standing astride with his or her legs spread.

The posture illustrated in FIG. 7 shows that the movement assistance device 1 is fitted onto the wearer without hindering his or her movement. Specifically, the back frame 11 rotates with respect to the back plate 10 and furthermore, the side frame 12 and the thigh holding portion 14 rotate with respect to the back frame 11, according to inclination of the body and the spread of the thighs of the wearer. As a result, the drive portion 13 contacts the vicinity of the side waist of the wearer, and the thigh holding portion 14 contacts the thigh of the wearer without separation. Therefore, the movement assistance device 1 can generate force that raises the upper body by driving the motor of the drive portion 13 and thus can assist the movement of the wearer.

Furthermore, since the shoulder belt 15 and the waist belt 18 for fixing the back plate 10, the back frame 11, and the waist plate 17 to the wearer are flexible members, the shape of the shoulder belt 15 and the waist belt 18 can be changed according to a change in the shape of the body of the wearer when the upper body of the wearer is twisted. With this, it is possible to avoid hindering the free movement of the wearer.

FIGS. 8(*a*) and 8(*b*) illustrate the second exemplary attitude of the movement assistance device 1 according to the present embodiment. The wearer illustrated in FIG. 8(*a*) assumes a level-shoulders posture. In contrast, the wearer illustrated in FIG. 8(*b*) assumes a posture with shoulders higher on the right side than on the left side.

Note that the shape of a back plate 10A illustrated in FIGS. 8(*a*) and 8(*b*) is different from the shape of the back plate 10 illustrated, for example, in FIG. 1, but the functions of the back plate 10A are substantially the same as those of the back plate 10.

As illustrated in FIG. 8(*b*), when the wearer changes his or her posture to raise one of his or her shoulders, the angle of rotation of the back frame 11 with respect to the back plate 10A changes. As the angle of rotation of the back frame 11 changes, the positions and angles of the side frame 12, the drive portion 13, and the thigh holding portion 14, etc., connected to the back frame 11 also change.

At this time, the angle of rotation of the back frame 11 with respect to the back plate 10A is restricted to an angle within the hollow part of the tubular restricting portion 171, and therefore the back frame 11 is prevented from being separated off from the inside of the restricting portion 171.

Note that even when the wearer twists his or her body at the same time as raising one of his or her shoulders, the rotation of the back frame 11 with respect to the back plate 10 and the rotation of the side frame 12 with respect to the back frame 11 allow the drive portion 13 and the thigh holding portion 14 to be maintained in positions that are not away from the body of the wearer.

As described above, the movement assistance device according to an aspect of the present invention can independently rotate the back frame with respect to the back plate and rotate the side frame with respect to the back frame according to the movement of the wearer. Thus, even when the wearer moves to twist his or her upper body or moves to swing his or her body so as to change the height of his or her left and right shoulders, the movement assistance device can follow the movement of the wearer without restricting the movement and, as necessary, assist the movement. Thus, the movement assistance device is capable of assisting the movement of the wearer while maintaining the degree of freedom of the movement.

Furthermore, the side frame is more stably supported with respect to the back frame and can follow the movement of the wearer. Thus, the movement assistance device is capable of assisting the movement of the wearer while maintaining the degree of freedom of the movement.

Furthermore, since the lower end of the back frame abuts the waist plate, the waist plate can prevent the lower end of the back frame from directly contacting the waist of the wearer. Thus, the back frame can rotate more smoothly, and the discomfort for the wearer, such as pressure and pain, upon fitting can be reduced.

Furthermore, with the angle of rotation of the back frame set within a predetermined range, the drive portion and the thigh holding portion connected to the back frame via the side frame can be maintained in positions that are not away from the body of the wearer. Thus, the movement assistance device is capable of assisting the movement of the wearer while maintaining the degree of freedom of the movement.

Furthermore, in the case where the posture of the wearer changes from a predetermined posture (for example, the standing posture) and then returns to the predetermined posture, the movement assistance device can return the angle of rotation of each of the back frame and the side frame to that for the original, predetermined posture. In the case where the wearer changes his or her posture and then returns to the original posture, the angle of rotation of the movement assistance device 1 returns to the original angle as well, and thus the wearer does not need to perform other special movements or operations. Thus, the movement assistance device is capable of assisting the movement of the wearer while maintaining the degree of freedom of the movement.

Furthermore, the movement assistance device transmits, to the belt and so on, force generated by the drive portion, to raise the upper body of the wearer to an upright position, and thus assists the movement of the wearer.

Furthermore, the wearer is fitted with the movement assistance device in such a manner as to support the weight of the movement assistance device, and the movement of the wearer is assisted by the movement assistance device. Thus, the movement assistance device is capable of simpler and easier assistance on the movement of the wearer while maintaining the degree of freedom of the movement.

Embodiment 2

The present embodiment describes the movement assistance device that improves the degree of freedom of a movement of a wearer, with a technique of increasing the degree of fitting tightness between the movement assistance device and the body of the wearer to more efficiently transmit, to the body of the wearer, force generated by the movement assistance device.

Figure 9:
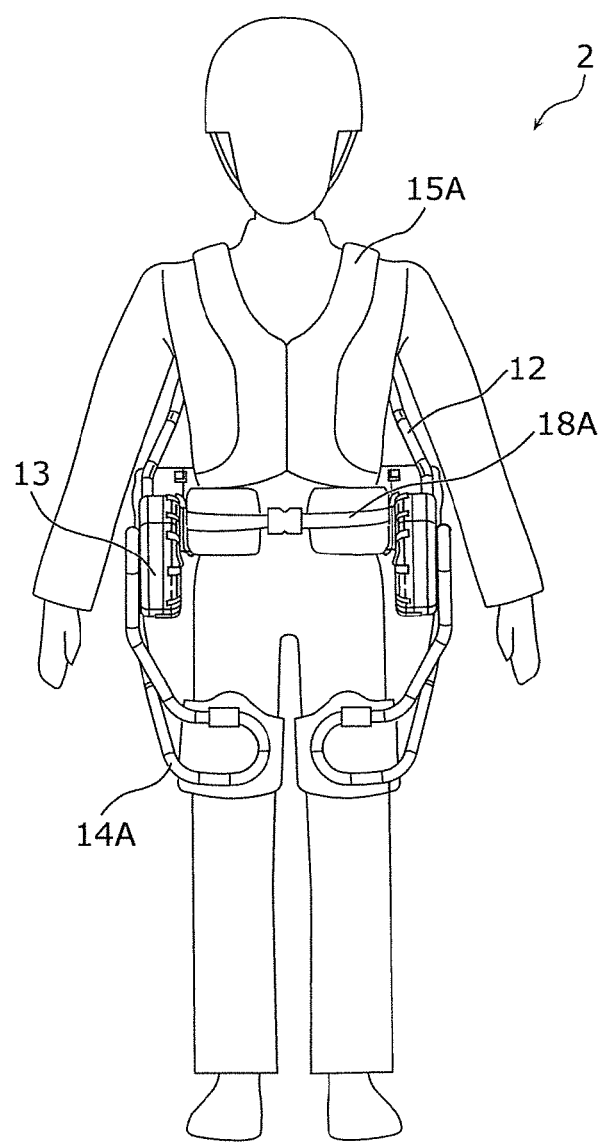
FIG. 9 is a front view of a movement assistance device according to Embodiment 2.

FIG. 9 is a front view of a movement assistance device 2 according to the present embodiment.

As illustrated in FIG. 9, the movement assistance device 2 includes a shoulder belt 15A, a waist belt 18A, and a thigh holding portion 14A. Among the elements included in the movement assistance device 2, the other elements are the same as those in Embodiment 1 and thus, detailed description thereof will be omitted.

The shoulder belt 15A, the waist belt 18A, and the thigh holding portion 14A have substantially the same configurations as the shoulder belt 15, the waist belt 18, and the thigh holding portion 14 in Embodiment 1, respectively, but have cushioning properties at the surfaces that contact the body of the wearer and thus have higher fitting tightness to the body of the wearer than those in Embodiment 1. Each of these elements will be described in detail below.

Figure 10:
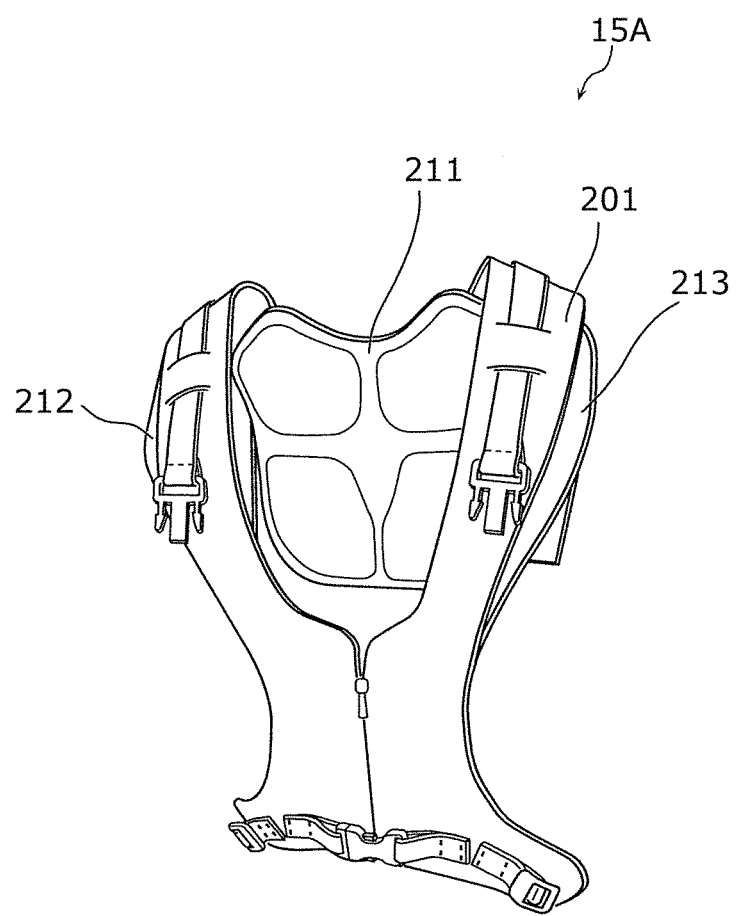
FIG. 10 is an external view of a shoulder belt according to Embodiment 2.
Figure 11:
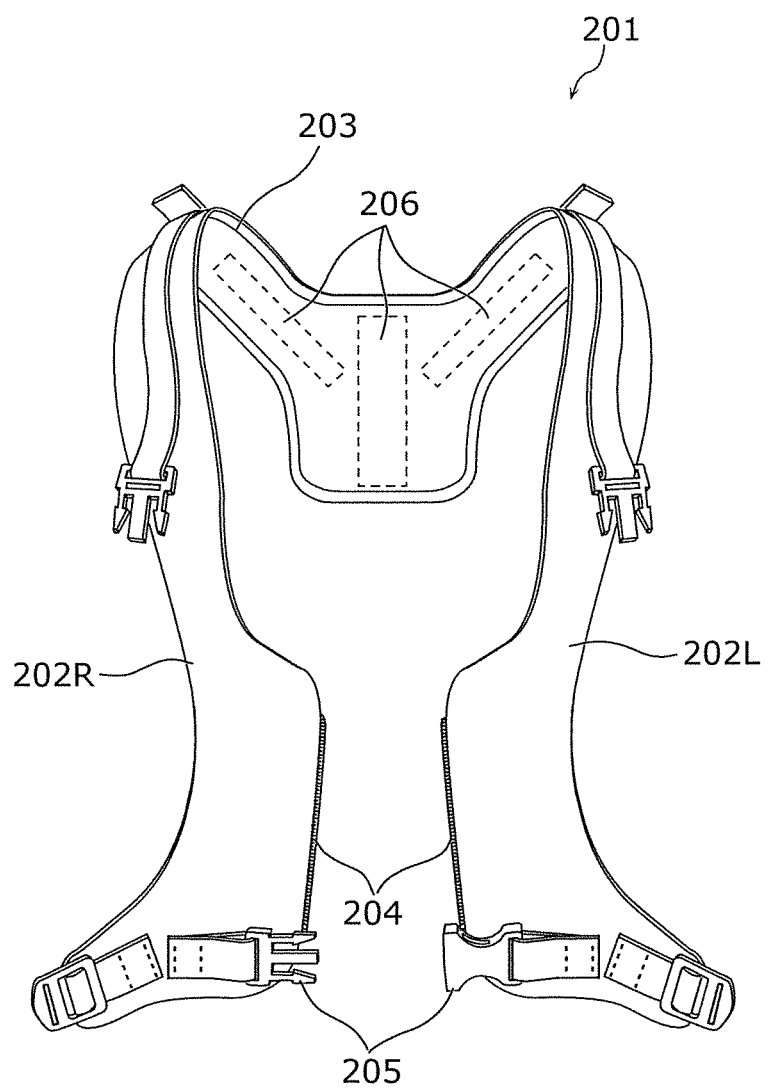
FIG. 11 is an external view of a shoulder belt main portion according to Embodiment 2.
Figure 12:
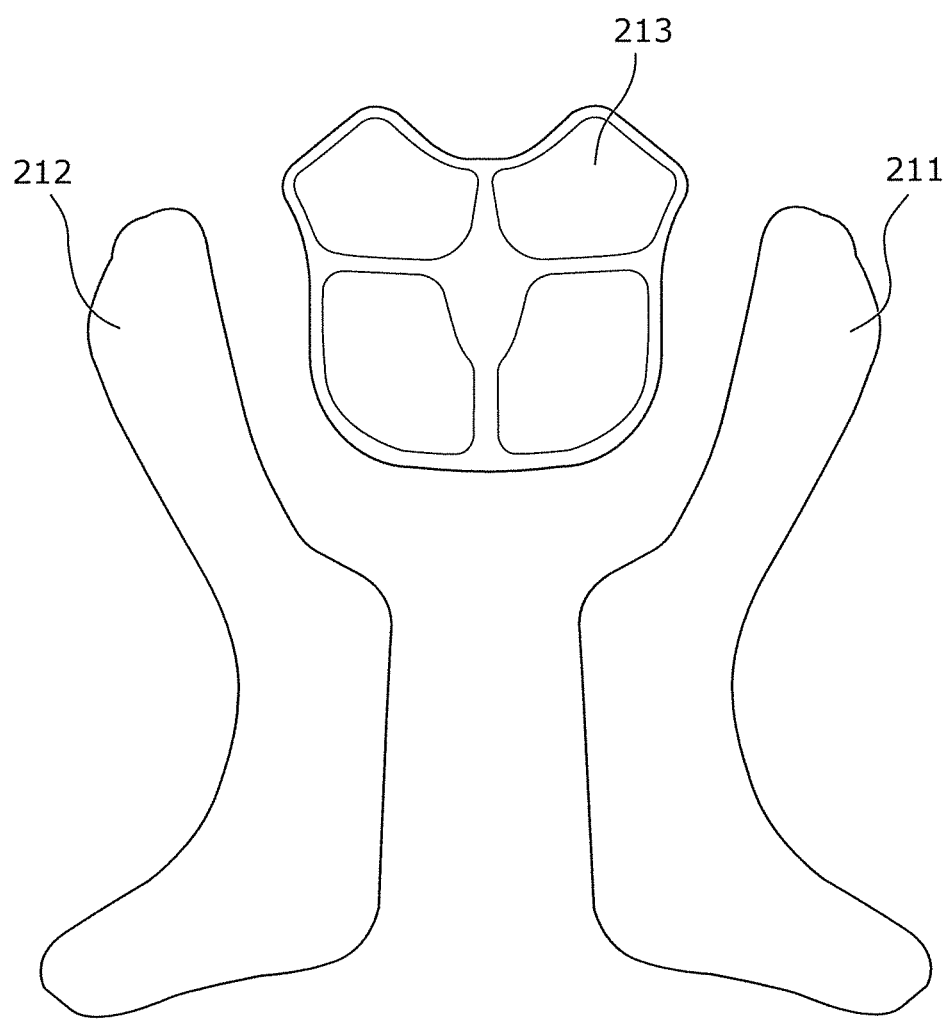
FIG. 12 is an external view of adjustment portions of a shoulder belt according to Embodiment 2.

FIG. 10 is an external view of the shoulder belt 15A according to the present embodiment. FIG. 11 is an external view of a shoulder belt main portion according to the present embodiment. FIG. 12 is an external view of adjustment portions of the shoulder belt according to the present embodiment. The shoulder belt 15A will be described with reference to these figures.

The shoulder belt 15A includes a shoulder belt main portion 201 and adjustment portions 211, 212, and 213.

The shoulder belt main portion 201, which is a main part of the shoulder belt 15A, is a band-shaped flexible member for maintaining the shape of the shoulder belt 15A. When the shoulder belt main portion 201 is fitted onto a wearer, the shoulder belt main portion 201 is curved to follow the shape of the body of the wearer. An attaching and detaching mechanism 206 for detachably attaching the adjustment portion 211, etc., is provided on a surface of the shoulder belt main portion 201 that faces the body of the wearer when the shoulder belt main portion 201 is fitted onto the wearer. The attaching and detaching mechanism 206 is a hook-and-loop faster, for example. Note that the attaching and detaching mechanism 206 may be a different element that performs the functions just described.

The shoulder belt main portion 201 includes a left belt 202L, a right belt 202R, and a back pad 203. In the state where the wearer is fitted with the shoulder belt main portion 201, the left belt 202L extends from the left shoulder of the wearer over the anterior surface of the body of the wearer to the waist belt 18A and is connected thereto, and the right belt 202R extends from the right shoulder of the wearer over the anterior surface of the body of the wearer to the waist belt 18A and is connected thereto. The back pad 203 is a portion that contacts the back of the wearer. The back plate 10 is positioned over the back of the wearer with the back pad 203 interposed therebetween.

The shoulder belt main portion 201 may include an attaching mechanism that allows the left belt 202L and the right belt 202R to detachably join together at the anterior surface of the body of the wearer. Examples of the attaching mechanism include a fastener 204 illustrated in FIG. 11 and an interlocking buckle 205. Note that aside from those just stated, a mechanism that uses a hook, snap, hook-and-loop fastener, button, lock, clasp and thread, or the like may be applied as the attaching mechanism. Since the shoulder belt main portion 201 includes the attaching mechanism as just described, it is possible to further increase the degree of fitting tightness of the shoulder belt 15A to the body of the wearer. With this, the force which the movement assistance device 2 generates for movement assistance is more efficiently transmitted to the body of the wearer, and thus the movement assistance performance improves, and wasteful force generation is reduced, producing the advantageous effect of reducing power consumption.

The adjustment portion 211 is a flexible member detachably attached to the left belt 202L. When the shoulder belt 15A abuts the body of the wearer, the adjustment portion 211 is positioned between the shoulder belt main portion 201 (the left belt 202L) and the body of the wearer, and further increases the degree of fitting tightness of the shoulder belt 15A to the body of the wearer. With this, the force which the movement assistance device 2 generates for movement assistance is more efficiently transmitted to the body of the wearer, and thus the movement assistance performance improves, and wasteful force generation is reduced, producing the advantageous effect of reducing power consumption. Furthermore, in the case where external impact is applied to the wearer via the shoulder belt 15A, such impact can be mitigated. In addition, the pressure from the shoulder belt 15A on the body of the wearer can be reduced.

The adjustment portion 212 is a flexible member detachably attached to the right belt 202R. The adjustment portion 213 is a flexible member detachably attached to the back pad 203. The adjustment portions 212 and 213 have substantially the same functions as the adjustment portion 211.

Note that the adjustment portions 211, 212, and 213 correspond to the first adjustment portion.

Note that the adjustment portion 211, etc., may be a cushioning member. With this, it is possible to further improve the advantageous effect such as an improvement in the properties of transmitting force generated by the movement assistance device 2, an improvement in the movement assistance performance, a reduction in the power consumption, or impact mitigation.

Note that the surface of the adjustment portion 211, etc., that faces the body of the wearer may be processed for allowing air to pass, for example, with a mesh pattern. This allows the wearer to sweat less and leads to a reduction in the production of sweat smell, and thus it is possible to improve the comfort for the wearer.

Note that as a result of being able to be attached to and detached from the shoulder belt main portion 201, the adjustment portion 211, etc., is removable from the shoulder belt main portion 201 for washing. Thus, the adjustment portion 211, etc., can be kept clean, and the comfort for the wearer is improved.

Note that generally, a portion that faces the body of the wearer is easily worn or damaged due to friction against clothing or the like of the wearer. This means that in the movement assistance device 2, the adjustment portion 211, etc., is easily worn or damaged. Since the adjustment portion 211, etc., can be attached to and detached from the shoulder belt main portion 201, the advantageous effect of allowing the movement assistance device 2 to be usable for a long period of time by replacing the adjustment portion 211, etc., with a new one is obtained.

Note that the size, shape, attachment position, and so on of the adjustment portion 211, etc., illustrated in FIG. 12 and other figures are a mere example; various modifications including a larger one, a smaller one, and one in a different shape are possible. The wearer can select a fitting portion that is to be used as the adjustment portion 211, etc., from among fitting portions of various sizes, shapes, and materials according to his or her body shape, the type of work to be performed with assistance from the movement assistance device, his or her preferences, or the like.

Figure 13:
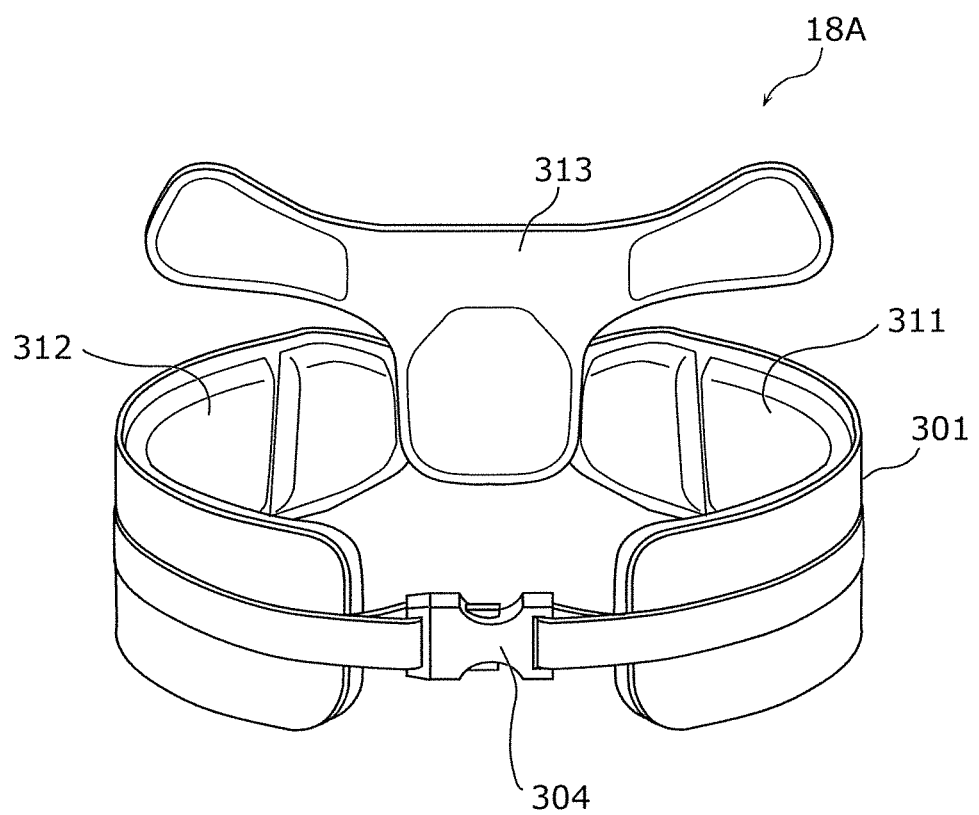
FIG. 13 is an external view of a waist belt according to Embodiment 2.
Figure 14:
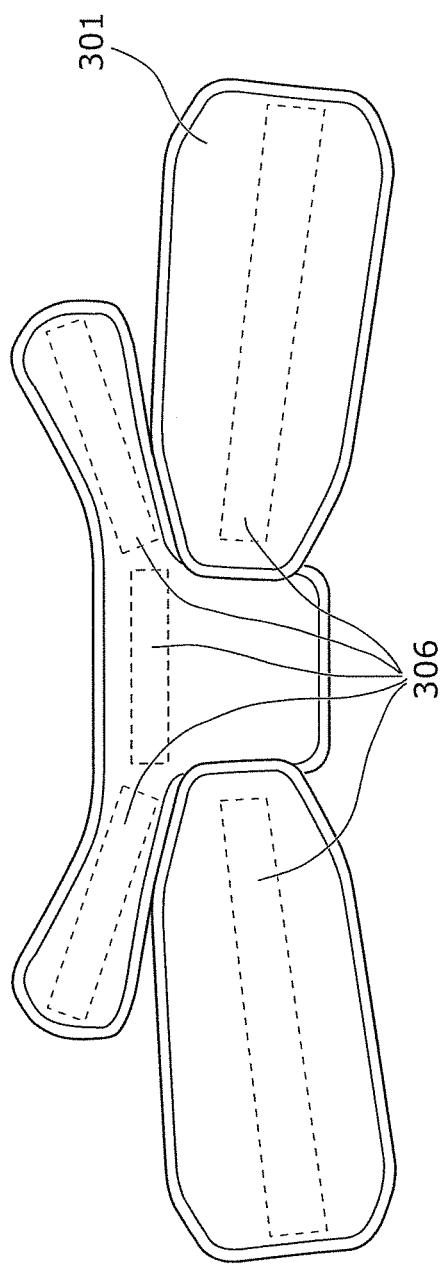
FIG. 14 is an external view of a waist belt main portion according to Embodiment 2.
Figure 15:
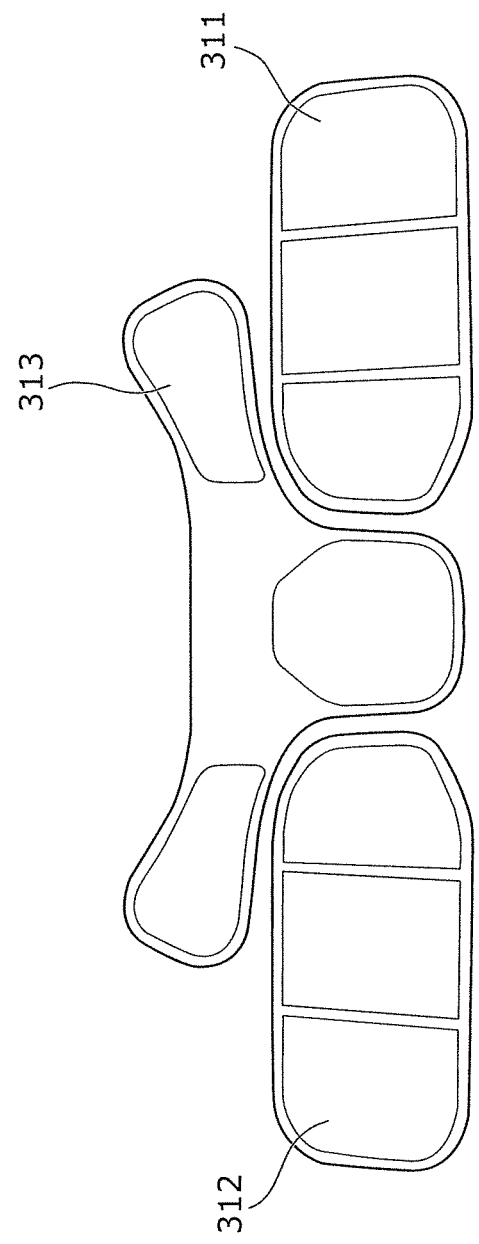
FIG. 15 is an external view of adjustment portions of a waist belt according to Embodiment 2.

FIG. 13 is an external view of the waist belt 18A according to the present embodiment. FIG. 14 is an external view of a waist belt main portion according to the present embodiment. FIG. 15 is an external view of an adjustment portion of the waist belt according to the present embodiment. The waist belt 18A will be described with reference to these figures.

The waist belt 18A includes a waist belt main portion 301 and adjustment portions 311, 312, and 313.

The waist belt main portion 301, which is a main part of the waist belt 18A, is a band-shaped flexible member for maintaining the shape of the waist belt 18A. When the waist belt main portion 301 is fitted onto a wearer, the waist belt main portion 301 is curved to follow the shape of the body of the wearer. An attaching and detaching mechanism 306 for detachably attaching the adjustment portion 311, etc., is provided on a surface of the waist belt main portion 301 that faces the body of the wearer when the waist belt main portion 301 is fitted onto the wearer. The attaching and detaching mechanism 306 is substantially the same as the attaching and detaching mechanism 206.

The waist belt main portion 301 is a band-shaped flexible member that is fitted around the waist of the wearer. The waist belt main portion 301 includes a connecting mechanism 304 that detachably connects the both ends of the waist belt 18A to each other at a position that is on the anterior surface of the body of the wearer when the waist belt main portion 301 is fitted onto the wearer. The wearer can easily wear and remove the waist belt 18A by switching between connection and disconnection of the both ends of the waist belt 18A with use of the connecting mechanism 304. The connecting mechanism 304 is an interlocking buckle, for example.

The waist plate 17 is attached to a central part of the waist belt main portion 301. In other words, the waist belt main portion 301 is connected to the waist plate 17.

The adjustment portion 311 is a flexible member that is detachably attached to a part of the waist belt main portion 301 that faces the left-side waist of the wearer. The adjustment portion 312 is a flexible member that is detachably attached to a part of the waist belt main portion 301 that faces the right-side waist of the wearer. The adjustment portion 313 is a flexible member that is detachably attached to a part of the waist belt main portion 301 that faces the waist of the wearer. The adjustment portions 311, 312, and 313 have substantially the same functions as the adjustment portion 211, etc.

Note that the adjustment portions 311, 312, and 313 correspond to the second adjustment portion.

Figure 16:
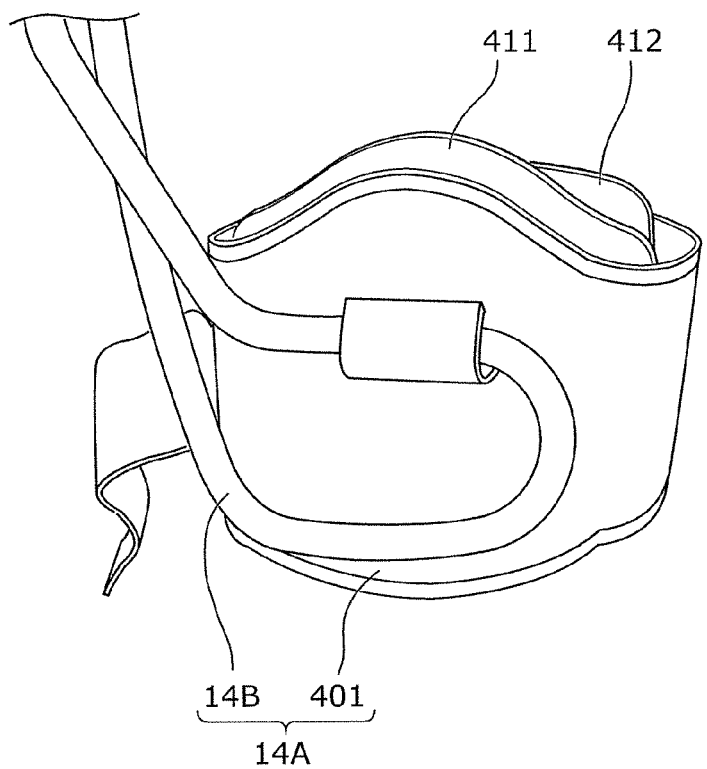
FIG. 16 is an external view of a thigh holding portion according to Embodiment 2.
Figure 17:
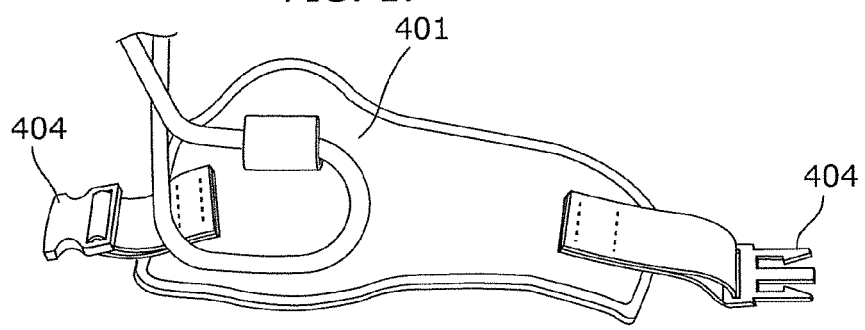
FIG. 17 is an external view of a thigh holding main portion according to Embodiment 2.
Figure 18:
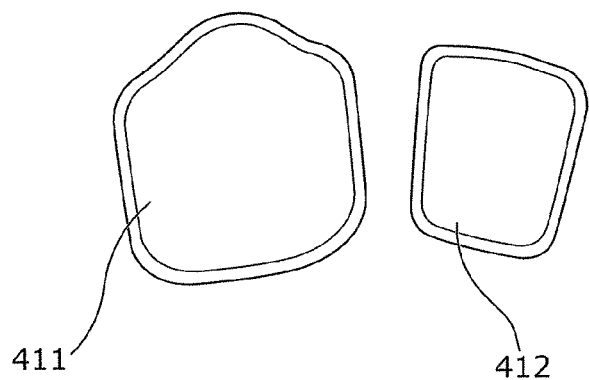
FIG. 18 is an external view of adjustment portions of a thigh holding portion according to Embodiment 2.

FIG. 16 is an external view of the thigh holding portion 14A according to the present embodiment. FIG. 17 is an external view of holding members for the thigh holding portion 14A according to the present embodiment. FIG. 18 is an external view of adjustment portions for the thigh holding portion 14A according to the present embodiment. The thigh holding portion 14A will be described with reference to these figures.

The thigh holding portion 14A includes a thigh holding main portion 14B, a thigh fitting portion 401, and adjustment portions 411 and 412.

The thigh holding main portion 14B is the same as the thigh holding portion 14 in Embodiment 1.

The thigh fitting portion 401 is connected to the thigh holding main portion 14B and is a flexible member that is fitted onto the thigh of the wearer. When the thigh fitting portion 401 is fitted onto a wearer, the thigh fitting portion 401 is curved to follow the shape of the thigh of the wearer. An attaching and detaching mechanism (not illustrated in the drawings) for detachably attaching the adjustment portion 411, etc., is provided on a surface of the thigh fitting portion 401 that faces the thigh of the wearer when the thigh fitting portion 401 is fitted onto the wearer. The attaching and detaching mechanism just described is substantially the same as the attaching and detaching mechanism 206, etc.

The thigh fitting portion 401 is a band-shaped flexible member that is fitted onto the thigh of the wearer. For example, the thigh fitting portion 401 is wound around the thigh of the wearer and thus fitted onto the wearer. With this, even when the body of the wearer moves, the thigh holding main portion 14B follows the movement of the body of the wearer, and thus force generated by the movement assistance device 2 can be transmitted to the wearer.

The thigh fitting portion 401 includes a connecting mechanism 404 that detachably connects the both ends of the thigh fitting portion 401 to each other. The wearer can easily wear and remove the thigh fitting portion 401 by switching between connection and disconnection of the both ends of the thigh fitting portion 401 with use of the connecting mechanism 404. The connecting mechanism is an interlocking buckle, for example.

The adjustment portion 411 is a flexible member that is detachably attached to a part of the thigh fitting portion 401 that faces the anterior thigh (the front part of the thigh) of the wearer. The adjustment portion 412 is a flexible member that is detachably attached to a part of the thigh fitting portion 401 that faces the posterior thigh (the rear part of the thigh) of the wearer. The adjustment portions 411 and 412 have substantially the same functions as the adjustment portion 211, etc.

Note that the adjustment portions 411 and 412 correspond to the third adjustment portion.

With the configuration described above, it is possible to improve the advantageous effect such as an improvement in the properties of transmitting force generated by the movement assistance device 2, an improvement in the movement assistance performance, a reduction in the power consumption, or impact mitigation.

Note that instead of the above-described configuration, the shoulder belt 15A may include a first belt that extends from the left shoulder of the wearer over the anterior surface of the body of the wearer to the right-side waist of the wearer and a second belt that extends from the right shoulder of the wearer over the anterior surface of the body of the wearer to the left-side waist of the wearer, and have what is called a crossed-belt configuration in which the first shoulder belt and the second shoulder belt cross each other at the anterior surface of the body of the wearer.

Although the movement assistance device in the present invention is described thus far based on the embodiments, the present invention is not limited to the embodiments. Various modifications of the present embodiment as well as embodiments resulting from combinations of structural elements of the different embodiments that may be conceived by those skilled in the art may be included within the scope of the present invention as long as these do not depart from the essence of the present invention.

INDUSTRIAL APPLICABILITY

The movement assistance device according to an aspect of the present invention is capable of assisting a movement of a wearer while maintaining the degree of freedom of the movement.

The invention claimed is:

1. A movement assistance device, comprising:
a back plate to be fitted onto a back of a wearer;
a back frame having an elongated shape and supported by a rotating shaft so as to be rotatable in a plane parallel to the back plate, the back frame including two first frame portions that rotate independently from each other, the rotating shaft being fixed to the back plate;
a side frame rotatably supported by a rotating shaft and extends from the back frame toward a vicinity of a side waist of the wearer, the side frame including two second frame portions that rotate independently from each other, each of the two second frame portions being supported by a respective one of the two first frame portions, the rotating shaft being fixed to the back frame and parallel to a longitudinal direction of the back frame;

a thigh holding portion to be fitted onto an anterior thigh of the wearer; and a drive portion connected to each of the side frame and the thigh holding portion, the drive portion being configured to generate a force that increases an angle between the side frame and the thigh holding portion.

2. The movement assistance device according to claim 1, wherein each of the two second frame portions of the side frame is rotatably supported by the back frame at both ends of the respective one of the two first frame portions of the back frame and rotates around an axis connecting both ends of the back frame as the rotating shaft.

3. The movement assistance device according to claim 1, further comprising a waist plate connected to the back plate via a flexible member and fitted onto a posterior waist of the wearer, wherein a lower end of the back frame abuts the waist plate.

4. The movement assistance device according to claim 3, wherein the waist plate includes a restricting portion configured to restrict an angle of rotation of the back frame with respect to the back plate to an angle within a predetermined range.

5. The movement assistance device according to claim 1, wherein the back frame includes a restoring mechanism configured such that, when an angle of rotation between the back frame and the side frame deviates from a predetermined range, the restoring mechanism changes the angle of rotation so that the angle of rotation falls within the predetermined range.

6. The movement assistance device according to claim 3, further comprising a shoulder belt to extend from the back plate over an anterior surface of a body of the wearer to the waist plate and connected to the waist plate, wherein the drive portion is configured to generate the force to increase the angle between the side frame and the thigh holding portion to provide standing force to the wearer via the back frame, the back plate, and the shoulder belt, the standing force being a force for raising an upper body of the wearer to an upright position.

7. The movement assistance device according to claim 6, wherein the drive portion is configured to provide the standing force to the wearer in a state where the movement assistance device is fitted onto the wearer without contacting a ground.

8. The movement assistance device according to claim 6, wherein the shoulder belt includes:

a left shoulder belt to extend from the back plate over a left shoulder and the anterior surface of the body of the wearer to the waist plate, and is connected to the waist plate;

a right shoulder belt to extend from the back plate over a right shoulder and the anterior surface of the body of the wearer to the waist plate, and is connected to the waist plate; and an attaching portion detachably joining the left shoulder belt and the right shoulder belt together at the anterior surface of the body of the wearer.

9. The movement assistance device according to claim 6, wherein the shoulder belt includes:

a shoulder belt main portion; and an adjustment portion detachably attached to a surface of the shoulder belt main portion, the surface to be facing the wearer in a state where the movement assistance device is fitted onto the wearer.

10. The movement assistance device according to claim 9, wherein the adjustment portion is a cushioning member.

11. The movement assistance device according to claim 3, further comprising a waist belt having a band shape and being connected to the waist plate and fitted around a waist of the wearer, wherein the waist belt includes:

a waist belt main portion; and an adjustment portion detachably attached to a surface of the waist belt main portion, the surface to be facing the wearer in a state where the movement assistance device is fitted onto the wearer.

12. The movement assistance device according to claim 11, wherein the adjustment portion is a cushioning member.

13. The movement assistance device according to claim 1, wherein the thigh holding portion includes:

a thigh fitting portion to be fitted onto a thigh of the wearer; and an adjustment portion detachably attached to a surface of the thigh fitting portion, the surface to be facing the wearer in a state where the movement assistance device is fitted onto the wearer.

14. The movement assistance device according to claim 13, wherein the adjustment portion is a cushioning member.

* * * * *